(12) United States Patent
Woolard et al.

(10) Patent No.: US 8,173,577 B2
(45) Date of Patent: May 8, 2012

(54) USE OF ABSCISIC ACID COMBINATIONS FOR THINNING

(75) Inventors: Derek D. Woolard, Zion, IL (US); Peter D. Petracek, Grayslake, IL (US); Michael Schroeder, Guggenhausen (DE); Johnny A. Lopez, Lubbock, TX (US); Schalk Reynolds, Grayslake, IL (US); Gregory Clarke, Dillsburg, PA (US); Prem Warrior, Green Oaks, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 403 days.

(21) Appl. No.: 12/011,806

(22) Filed: Jan. 30, 2008

(65) Prior Publication Data
US 2008/0254984 A1    Oct. 16, 2008

Related U.S. Application Data

(60) Provisional application No. 60/898,532, filed on Jan. 31, 2007, provisional application No. 60/898,631, filed on Jan. 31, 2007.

(51) Int. Cl.
*A01N 25/00* (2006.01)
(52) U.S. Cl. .................................. 504/116.1
(58) Field of Classification Search ............ 504/116.1
See application file for complete search history.

(56) References Cited

U.S. PATENT DOCUMENTS

| 5,163,993 A | 11/1992 | Shafer et al. |
| 5,173,106 A * | 12/1992 | Kamuro et al. ............... 504/320 |
| 2005/0198896 A1 * | 9/2005 | Quaghebeur ............ 47/58.1 FV |
| 2008/0318787 A1 * | 12/2008 | Quaghebeur ................ 504/142 |

FOREIGN PATENT DOCUMENTS
WO    WO 2006018266 A1  *  2/2006

OTHER PUBLICATIONS

Robert J. Weaver Growth regulators offer numerous benefits. California Agriculture, Jul. 1980 p. 28-29.*
JP 06100407, Falling Acceleration of Flowers, or Fruits by Spraying with Natural Type Abscisic Acid and Ethephon, Apr. 12, 1994, Derwent Abstract, pp. 1-2.*
Benzyladenine effects on fruit size, fruit thinning and return yield of 'Spadona' and 'Coscia' pear Stern et al. Scienta Horticulturae 98 (2003) 409-504.*
Kamuro et al. The promotive effect of applying mixtures of (S)-(+)-abscisic acid and gibberellic acid on flowering in long-day plants. Plant Growth Regulation 33: 189-194, 2001.*
Kende et al., "The five 'classical' plant hormones", The Plant Cell, Jul. 1997, vol. 9, pp. 1197-1210.
Ebert et al., "Possible hormonal modes of action of three applie thinning agents", Scientia Horticulture, 1982, vol. 16, pp. 343-356.
Cooper et al., "Induction of abscission at hypobaric pressures", Plant Physiology, 1973, vol. 51, pp. 1002-1004.
Petracek et al., "A history of commercial plant growth regulators in apple production", HortScience, 2003, vol. 38, pp. 937-942.
Milborrow, "Inhibitors", Advanced Plant Physiology, pp. 76-110.

* cited by examiner

*Primary Examiner* — Annette Para
(74) *Attorney, Agent, or Firm* — Wood, Phillips, Katz, Clark & Mortimer

(57) ABSTRACT

The present invention is directed to the treatment of a plant at the flowering or fruiting stage with an effective amount of abscisic acid, its analogs or derivatives and salts thereof to reduce the number of fruits that the plant sets and grows to maturity.

1 Claim, No Drawings

USE OF ABSCISIC ACID COMBINATIONS FOR THINNING

FIELD OF THE INVENTION

This invention relates to a novel method for reducing the number of fruits on plants by treating the plants with abscisic acid (ABA) and a gibberellin or abscisic acid and a cytokinin. Specifically, the invention relates to a method for selectively reducing the crop load of plants.

BACKGROUND OF THE INVENTION

Many plants set more fruits than is desirable for the production of high quality fruit of commercial size. Plants setting too many fruits can lead to each fruit being smaller than if the fruit set is reduced, by a process called thinning.

Thinning of fruits, or the flowers that can become fruits, can be accomplished by hand removal of small fruits or flowers by hand thinning. Hand thinning is very costly and labor to complete the job can be difficult to obtain.

Chemical treatments have been used to commercially thin a variety of crops including apples and grapes. There are currently no effective chemical fruitlet thinners for stone fruit. Chemical thinners are sometimes not effective due to under thinning, over thinning, chemical burns due to phytotoxicity, inhibition of fruit growth and abscission of leaves. For example, a chemical thinner that induces indiscriminate abscission of leaves and fruit would be of no commercial value. Consequently, there is a need for improved chemical thinning agents.

The use of gibberellic acid ($GA_3$) to thin seedless grapes is an industry standard. However, enhanced thinning of seedless grapes under some circumstances may be desirable. Also, $GA_3$ use on seeded grapes is not common due to the potential for reduced bloom density during the following season as a result of the $GA_3$ treatment. Addition of another chemical thinning agent with $GA_3$ could allow for adequate thinning of seeded grapes at lower $GA_3$ rates and thus lower the potential for $GA_3$-induced reduction of bloom density the following year.

The use of benzyladenine (BA) to thin apples is an industry standard. However, enhanced thinning of some apple varieties may be desirable. Addition of another chemical thinning agent with BA could permit adequate apple thinning.

ABA is a naturally-occurring hormone found in all higher plants (Cutler and Krochko, 1999, Trends in Plant Science, 4:472-478; Finkelstein and Rock, 2002. The *Arabidopsis* Book. ASPB, Monona, Md., 1-52). Endogenous ABA is involved in a number of physiological processes including modulation of germination, dormancy, stomatal conductance, plant growth, and leaf abscission (Milborrow, 1984, in Plant Physiology, ed Wilkins, 76-110; Kende and Zeevaart, 1997, Plant Cell, 9:1197-1210).

Quaghebeur (2005, US Patent Application No. 20050198896 A1) speculated that ABA causes defoliation, bloom inhibition, and fruit drop and induces hibernation-like states. The uses for ABA on fruit trees described in Quaghebeur (2005) are limited to enhancing leaf removal, reducing cherry cracking, and reducing burgeoning growth caused by rain. When using ABA on apples and pears according to Quaghebeur (2005), quick leaf abortion is observed and airflow through the tree is improved. However, Quaghebeur (2005) does not mention the selective removal of flowers or young fruitlets preferentially over leaf defoliation and does not suggest the use of ABA as an effective thinning agent.

There are no published reports on the use of ABA as a thinning agent.

The use of the combination of $GA_3$ with ABA for thinning has not been previously reported.

The use of the combination of BA with ABA for thinning has not been previously reported.

SUMMARY OF THE INVENTION

The present invention is directed to the treatment of a plant with an effective amount of ABA or its salts, derivatives or analogs at the flowering or fruiting stage to reduce the number of fruits that the plant sets and grows to maturity.

More specifically, the invention relates to a method for applying to flowering or fruiting plants an effective amount of abscisic acid, its salts, derivatives or analogs alone or in combination with gibberellins such as gibberellic acid (GA3) or adenine-based cytokinins such as benzyladenine (BA) or urea-based cytokinins such as forchlorfenuron (CPPU) applied simultaneously or in sequential applications to reduce the number of fruits that set and mature on the plant.

DETAILED DESCRIPTION OF THE INVENTION

As used herein the term "ABA" refers to abscisic acid (S-ABA; ABA; S-(+)-abscisic acid; +-ABA, (+)-(S)-cis, trans-abscisic acid, (+)-(S)-cis,trans-ABA; S-ABA; (S)-5-(1-hydroxy-2,6,6,-trimethyl-4-oxo-2-cyclohexen-1-yl)-3-methyl-(2Z,4E)-pentadienoic acid; CAS registry no. [21293-29-8]).

As used herein, the term "salt" refers to the water soluble salts of ABA or ABA analogs or derivatives, as appropriate. Representative such salts include inorganic salts such as the ammonium, lithium, sodium, potassium, magnesium and calcium salts and organic amine salts such as the triethanolamine, dimethylethanolamine and ethanolamine salts.

Presently preferred ABA analogs and derivatives include PBI-429, PBI-524, PBI-696 and PBI-702.

For the purposes of this Application, abscisic acid analogs are defined by Structures 1, 2 and 3, wherein for Structure 1:
the bond at the 2-position of the side chain is a cis- or trans-double bond,
the bond at the 4-position of the side chain is a trans-double bond or a triple bond,
the stereochemistry of the alcoholic hydroxyl group is S—, R— or an R,S— mixture,
the stereochemistry of the R1 group is in a cis-relationship to the alcoholic hydroxyl group,
R1=ethynyl, ethenyl, cyclopropyl or trifluoromethyl, and
R2=hydrogen or lower alkyl

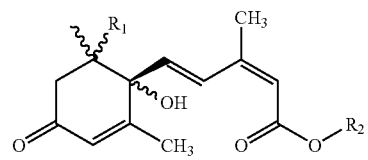

Structure 1 wherein lower alkyl is defined as an alkyl group containing 1 to 4 carbon atoms in a straight or branched chain, which may comprise zero or one ring or double bond when 3 or more carbon atoms are present.

For PBI-429, R1 is ethynyl and R2 is a methyl group.
For PBI-524, R1 is ethynyl and R2 is a hydrogen.
For PBI-696, R1 is cyclopropyl and R2 is a methyl group.

For Structure 2:
the bond at the 2-position of the side chain is a cis- or trans-double bond,
the bond at the 4-position of the side chain is a triple bond,
the stereochemistry of the alcoholic hydroxyl group is S—, R— or an R,S— mixture,
R1=hydrogen or lower alkyl

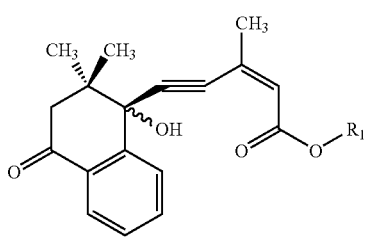

Structure 2 wherein lower alkyl is defined as an alkyl group containing 1 to 4 carbon atoms in a straight or branched chain, which may comprise zero or one ring or double bond when 3 or more carbon atoms are present.

For PBI-702, R1 is a methyl group.
For Structure 3:
the bond at the 2-position of the side chain is a cis- or trans-double bond,
the bond at the 4-position of the side chain is a trans-double bond,
the stereochemistry of the alcoholic hydroxyl group is S—, R— or an R, S— mixture,
R1=hydrogen or lower alkyl

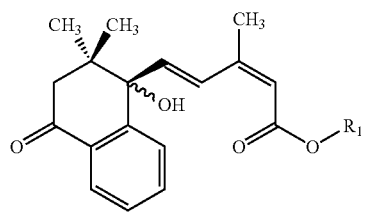

Structure 3 wherein lower alkyl is defined as an alkyl group containing 1 to 4 carbon atoms in a straight or branched chain, which may comprise zero or one ring or double bond when 3 or more carbon atoms are present.

It is also contemplated that salts of the ABA analogs set forth above may be utilized in accordance with the present invention.

The applied concentration of ABA or its salts, derivatives or analogs can vary widely depending on the water volume applied to plants as well as other factors such as plant age and size, and plant sensitivity to ABA, but is generally in the range of about 1 ppm to about 10,000 ppm, preferably from about 10 to about 2000 ppm, and more preferably about 50 to about 1000 ppm.

For grape thinning, the applied concentration of $GA_3$ can vary widely depending on the water volume applied to plants as well as other factors such as plant age and size, and plant sensitivity to $GA_3$, but is generally in the range of about 1 to about 1000 ppm and preferably from about 2 to about 100 ppm.

For apple thinning, the applied concentration of BA can vary widely depending on the water volume applied to plants as well as other factors such as plant age and size, and plant sensitivity to BA, but is generally in the range of about 1 to about 300 ppm and preferably from about 20 to about 150 ppm.

Other ingredients such as surfactants can be utilized in compositions useful in the present invention.

The presently preferred surfactant for ABA performance is Brij 98 (polyoxyethylene (20) oleyl ether) available from Uniqema (Castle, Del.). Other surfactants are also useful in the present invention, including but not limited to: other surfactants in Brij family (polyoxyethylene fatty alcohol ether) from Uniqema (Castle, Del.); surfactant in Tween family (Polyoxyethylene sorbitan esters) from Uniqema (Castle, Del.); Silwet family (Organosilicone) from Union Carbide (Lisle, Ill.); Triton family (Octylphenol ethoxylate) from The Dow Chemical Company (Midland, Mich.); Tomadol family (ethoxylated linear alcohol) from Tomah3 Products, Inc. (Milton, Wis.); Myrj family (Polyoxyethylene (POE) fatty acid esters) from Uniqema (Castle, Del.); Span family (Sorbitan ester) from Uniqema (Castle, Del.); and Trylox family (Ethoxylated Sorbitol and Ethoxylated Sorbitol Esters) from Cognis Corporation (Cincinnati, Ohio) as well as commercial surfactant Latron B-1956 (77.0% modified phthalic/glycerol alkyl resin and 23.0% Butyl alcohol) from Rohm & Haas (Philadelphia, Pa.); Caspil (Blend of Polyether-polymethyl-siloxanecopolymer and nonionic surfactant) from Aquatrols (Paulsboro, N.J.); Agral 90 (Nonyl phenol ethoxylate) from Norac Concept. Inc. (Orleans, Ontario, Canada); Kinetic (99.00% Proprietary blend of polyalkyleneoxide modified polydimethylsiloxane and nonionic surfactants) from Setre Chemical Company (Memphis, Tenn.); and Regulaid (90.6% 2-butoxyethanol, poloxalene, monopropylene glycol) from KALO, Inc. (Overland Park, Kans.).

The present invention is illustrated by the following representative, but non-limiting examples.

EXAMPLES

Example 1

Clusters of Cabernet Franc grapes were dipped at the full bloom stage with water, 10 ppm gibberellic acid ($GA_3$), 300 ppm abscisic acid (S-ABA; ABA; S-(+)-abscisic acid; +-ABA, (+)-(S)-cis,trans-abscisic acid, (+)-(S)-cis,trans-ABA; S-ABA; (S)-5-(1-hydroxy-2,6,6,-trimethyl-4-oxo-2-cyclohexen-1-yl)-3-methyl-(2Z,4E)-pentadienoic acid; CAS no. 21293-29-8) or ABA and $GA_3$ together. One cluster was tagged and treated with each of the treatments on each of 10 vines. The clusters were harvested at commercial maturity. Cluster compactness was assessed by counting the number of berries per cluster and measuring the total rachis length of each cluster and then calculating the number of berries per cm of rachis.

TABLE 1

Effect of dipping Cabernet Franc flower clusters at full bloom with 10 ppm $GA_3$, 300 ppm ABA or combination of $GA_3$ and ABA on berry number and cluster compactness.

| Treatment | Number of berries per cluster | Number of berries per cm rachis |
| --- | --- | --- |
| Water | 45.8 | 1.72 |
| 10 ppm $GA_3$ | 34.8 | 1.33 |
| 300 ppm ABA | 53.0 | 1.87 |
| $GA_3$ + ABA | 23.3 | 0.88 | n = 10 clusters per treatment

Dipping clusters in 10 ppm GA₃ reduced the number of berries per cluster and berries per cm of rachis compared to the water dipped control (Table 1). Dipping clusters in 300 ppm ABA had no effect or caused a slight increase in the number of berries per cluster and berries per cm of rachis compared to the water dipped control. Dipping clusters in 10 ppm GA₃ with 300 ppm ABA significantly reduced the number of berries per cluster and the number of berries per cm rachis compared to the water-dipped control, the GA₃-dipped clusters and the ABA-dipped clusters. The ABA did not thin the grape clusters in this Example, however addition of ABA to the GA₃ treatment caused more thinning than the GA₃ alone treatment.

Example 2

Clusters of Cabernet Franc grapes were dipped at the full bloom stage with water, 300 ppm ABA, 10 ppm GA₃ or 300 ppm ABA mixed with 10 ppm GA₃. One cluster was tagged and treated with each of the treatments on each of 10 vines. The clusters were harvested at commercial maturity and berry number and cluster compactness were evaluated.

TABLE 2

Effect of dipping Cabernet Franc flower clusters at full bloom with 10 ppm GA₃, 300 ppm ABA or combination of GA₃ and ABA on berry number and cluster compactness.

| Treatment | Number of berries per cluster | Number of berries per cm rachis |
|---|---|---|
| Water | 59.8 | 2.1 |
| 300 ppm ABA | 54.3 | 2.0 |
| 10 ppm GA₃ | 37.6 | 1.35 |
| 300 ppm ABA + GA₃ | 27.8 | 1.02 | n = 10 clusters per treatment

Dipping clusters in 10 ppm GA₃ reduced the number of berries per cluster and berries per cm of rachis compared to the water dipped control (Table 2). Dipping clusters in 300 ppm ABA had no effect on the number of berries per cluster and berries per cm of rachis compared to the water dipped control. Dipping clusters in 10 ppm GA₃ with 300 ppm ABA significantly reduced the number of berries per cluster and the number of berries per cm rachis compared to the water-dipped control, the GA₃-dipped clusters and the ABA-dipped clusters. The ABA did not thin the grape clusters in this Example, however addition of ABA to the GA₃ treatment caused more thinning than the GA₃ alone treatment. Application of ABA with GA₃ may allow for lower GA₃ rates that could reduce the likelihood of the vines of seeded grapes showing a GA₃-induced reduction in bloom density the year after treatment.

Example 3

Vines of Thompson Seedless grape were sprayed with GA₃ only or GA₃ combined with ABA; the spray was primarily directed to the flower clusters. The applications were made twice, once at 70% bloom and once at 100% bloom. Grape bunch compactness was rated at harvest and the average bunch mass and the average number of berries per gram of rachis was determined.

TABLE 3

Effect of GA₃ and GA₃ with ABA on Thompson Seedless Grapes

| Treatment | Bunch Compactness[1] | Average bunch mass (g) | Average number of berries per gram of rachis |
|---|---|---|---|
| GA₃ only | 2.3 | 830 | 5.7 |
| GA₃ + ABA | 1.7 | 582 | 5.0 |

[1]= Bunch Compactness Rating Scale - 1 = very loose bunch, 5 = very tight bunch Thompson Seedless grape vines treated with GA3 with ABA produced looser bunches than vines treated with GA₃ alone as shown by lower compactness rating and lower number of berries per gram of rachis (Table 3).

Example 4

Pioneer McIntosh apple trees were selected for uniformity of bloom and 2 limbs per tree were tagged and all blossom clusters on the tagged limbs were counted. Treatments were applied to four replicate trees per treatment when the average fruit size was 9 mm. BA at 75 ppm was applied as a dilute solution sprayed on whole trees to the drip point on two of the four trees in each replication. ABA was first mixed with ethanol to create a 10% wt/v stock solution. The solution was shaken and then allowed to sit for 5 minutes. The ABA/ethanol was then poured into a sprayer with water containing 0.75% Regulaid to result in a final concentration of 300 ppm ABA. Once the BA had dried the ABA was applied only to the tagged limbs on one tree that received no other sprays on one tree that had previously been sprayed with BA. The fourth tree in each block received no spray and served as the control. At the end of the June drop period in July, all fruit on the tagged limbs was counted and recorded.

TABLE 4

Effects of BA and ABA of fruit set of McIntosh apple trees

| Treatment | % Fruit Set | Average Fruit Weight, g |
|---|---|---|
| Untreated | 104 | 139 |
| 75 ppm BA | 75 | 190 |
| 300 ppm ABA | 25 | 146 |
| 75 ppm BA + 300 ppm ABA | 16 | 197 |

Application of BA reduced fruit set (Table 4). Application of ABA reduced fruit set more than BA reduced fruit set. Sequential application of BA and ABA reduced fruit set more than either ABA or BA alone. Application of BA or ABA increased fruit size, and sequential application of BA and ABA increased fruit size more than either treatment alone.

Example 5

Empire apple trees were selected for tree size and uniformity of bloom. Treatments were applied to five replicate trees per treatment when the average fruit size was 8 mm. BA at 100 ppm was applied as a dilute solution sprayed on whole trees to the drip point on five trees. Another five trees were sprayed with a mixture of 100 ppm BA and 1000 ppm ABA. Five trees were left untreated to act as control trees. At the end the season when the fruit were mature all the fruit were harvested and the number of fruit per tree and the average fruit size were determined.

TABLE 5

Effects of BA and ABA on crop load and fruit size of Empire apple trees

| Treatment | Number of Fruit per Tree | Average Fruit Weight, g |
| --- | --- | --- |
| Untreated | 169 | 107 |
| 100 ppm BA | 137 | 123 |
| 100 ppm BA + 1000 ppm ABA | 98 | 128 |

Application of BA reduced the number of fruit per tree and increased average fruit size (Table 5). Application of BA and ABA together reduced of fruit per tree and increased average fruit size more than BA alone. Surprisingly the inclusion of ABA, a reported growth inhibitor, increased fruit size.

These examples have shown that the addition of ABA to standard thinning treatments to have enhanced the selective thinning response over the standard thinning treatment alone for both grape and apple without inducing leaf drop or causing phytotoxic burns.

Example 6

European seedless cucumber (var. *Flamingo*) plants were grown in a greenhouse. At the 20 node growth stage the plants were sprayed to drip with ABA (100 ppm) solution or left unsprayed (control). ABA treated plants had twice the rate of fruit abortion compared to the control plants (Table 8). This example shows that ABA can selectively reduce crop load without inducing fruit abscission.

TABLE 6

Effect of foliar sprays with ABA on abortion of cucumber fruits.

| Treatment | Percentage of basal 18 cucumber fruits per plant that aborted |
| --- | --- |
| Control | 34 |
| ABA | 68 |

* n = 5 replicate plants per treatment.

The invention claimed is:

1. A method of thinning flowers and fruits on grape plants comprising applying about 300 ppm of at least one of S-(+)-abscisic acid, a salt, an analog or a derivative thereof and about 10 ppm of at least one of gibberellin, a salt, an analog or a derivative thereof, to a grape plant.

* * * * *